United States Patent
Dutta et al.

(10) Patent No.: US 11,977,608 B2
(45) Date of Patent: May 7, 2024

(54) METHOD AND SYSTEM FOR REAL-TIME SHELF-LIFE PREDICTION OF FOOD ITEMS

(71) Applicant: Tata Consultancy Services Limited, Mumbai (IN)

(72) Inventors: Jayita Dutta, Pune (IN); Parijat Deshpande, Pune (IN); Manasi Samarth Patwardhan, Pune (IN); Shirish Subhash Karande, Pune (IN); Shankar Kausley, Pune (IN); Priya Kedia, Pune (IN); Shrikant Arjunrao Kapse, Pune (IN); Beena Rai, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 435 days.

(21) Appl. No.: 17/515,834

(22) Filed: Nov. 1, 2021

(65) Prior Publication Data
US 2022/0147755 A1    May 12, 2022

(30) Foreign Application Priority Data
Nov. 6, 2020  (IN) .............................. 202021048601

(51) Int. Cl.
*G06N 3/045*   (2023.01)
*G01N 33/02*   (2006.01)
(Continued)

(52) U.S. Cl.
CPC ......... *G06F 18/2413* (2023.01); *G01N 33/02* (2013.01); *G06F 18/214* (2023.01);
(Continued)

(58) Field of Classification Search
CPC .... G06F 18/2413; G06F 18/214; G06F 18/22; G01N 33/02; G06T 7/001;
(Continued)

(56) References Cited

U.S. PATENT DOCUMENTS 7,603,330 B2    10/2009 Gupta et al.
2016/0148149 A1*   5/2016 Suddamalla ......... G06Q 10/087
                                                            705/28

OTHER PUBLICATIONS

R. Dandavate and V. Patodkar, "CNN and Data Augmentation Based Fruit Classification Model," 2020 Fourth International Conference on I-SMAC (IoT in Social, Mobile, Analytics and Cloud) (I-SMAC), Palladam, India, 2020, pp. 784-787, doi: 10.1109/I-SMAC49090.2020.9243440. (Year: 2020).*

(Continued)

*Primary Examiner* — Bobbak Safaipour
*Assistant Examiner* — Ashley L. Hytrek
(74) *Attorney, Agent, or Firm* — Finnegan, Henderson, Farabow, Garrett & Dunner LLP

(57) ABSTRACT

Traditional food quality monitoring systems fail to monitor the variation of food quality in real-time scenarios. Existing machine learning approaches require dedicated data models for different classes of food items due to differences in characteristics of different food items. Also, to generate such data models, a lot of annotated data is required per food item, which are expensive. The disclosure herein generally relates to monitoring and shelf-life prediction of food items, and, more particularly, to system and method for real-time monitoring and shelf-life prediction of food items. The system generates a data model using a knowledge graph indicative of a hierarchical taxonomy for a plurality of categories of the plurality of food items, which in turn contains metadata representing similarities in physio-chemical degradation pattern of different classes of the food items. This data model serves as a generic data model for real-time shelf-life prediction of different food items.

12 Claims, 5 Drawing Sheets

(51) Int. Cl.
    *G06F 18/214*     (2023.01)
    *G06F 18/22*     (2023.01)
    *G06F 18/2413*     (2023.01)
    *G06N 5/02*     (2023.01)
    *G06N 20/10*     (2019.01)
    *G06N 20/20*     (2019.01)
    *G06T 7/00*     (2017.01)
    *G06V 10/84*     (2022.01)
    *G06V 20/68*     (2022.01)

(52) U.S. Cl.
    CPC .............. *G06F 18/22* (2023.01); *G06T 7/001* (2013.01); *G06T 2207/20081* (2013.01); *G06T 2207/30128* (2013.01); *G06V 20/68* (2022.01); *G06V 2201/10* (2022.01)

(58) Field of Classification Search
    CPC ........... G06T 2207/20081; G06T 2207/30128; G06V 20/68; G06V 2201/10
    See application file for complete search history.

(56) References Cited

OTHER PUBLICATIONS

Chilek et al., "A shelf life study: An evaluation on physicochemical properties and microbiological analysis of honey and Nigella sativa seed mixture during accelerated storage," Malays. Appl. Biol. 47(4): 107-116 (2018).
Valero et al., "Principles and Methodologies for the Determination of Shelf-Life in Foods," (2012).

\* cited by examiner

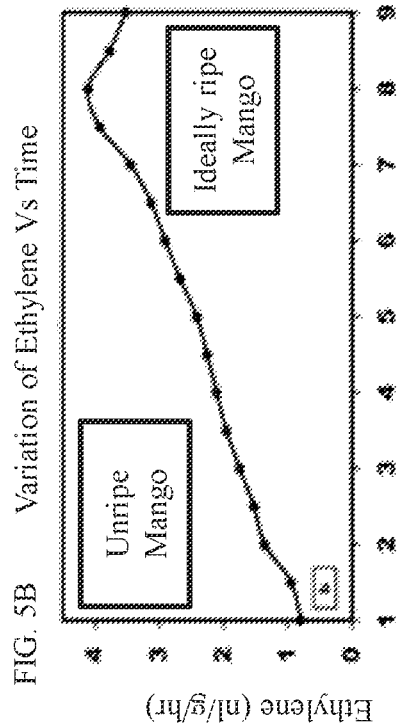
FIG. 5B Variation of Ethylene Vs Time
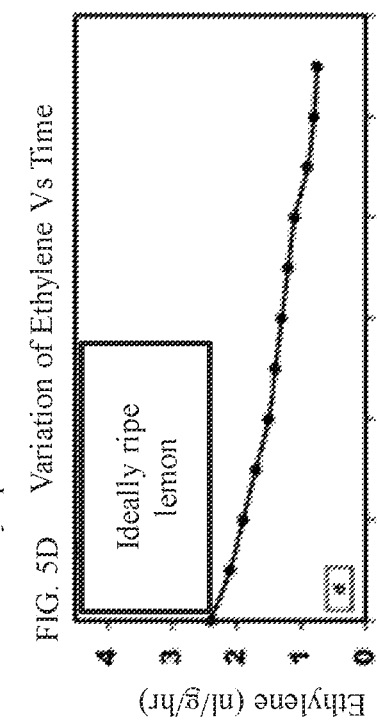
FIG. 5D Variation of Ethylene Vs Time
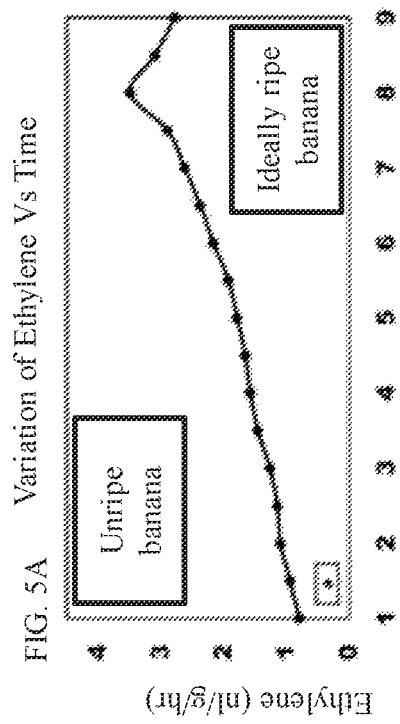
FIG. 5A Variation of Ethylene Vs Time
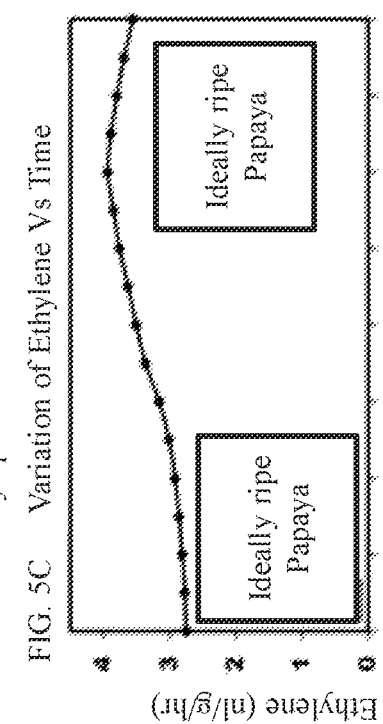
FIG. 5C Variation of Ethylene Vs Time

METHOD AND SYSTEM FOR REAL-TIME SHELF-LIFE PREDICTION OF FOOD ITEMS

PRIORITY CLAIM

This U.S. patent application claims priority under 35 U.S.C. § 119 to: India Application No. 202021048601, filed on Nov. 6, 2020. The entire contents of the aforementioned application are incorporated herein by reference.

TECHNICAL FIELD

The disclosure herein generally relates to monitoring and shelf-life prediction of food items, and, more particularly, to system and method for real-time monitoring and shelf-life prediction of food items.

BACKGROUND

Global food wastage is a big challenge today. According to Food and Agriculture Organization (FAO)—United Nations, worldwide food wastage accounts to 1.3 billion tons annually. The wastage occurs at every node of food supply chain starting from farms to consumers and is largely affected by the variation of environmental parameters over time. The food wastage has a considerable negative impact on our society, environment and world economy. One in every nine people in the world goes hungry, and also causes economic loss in the range of trillions of dollars.

The inventors here have recognized several technical problems with such conventional systems, as explained below. Main reason behind the food wastage is inability to monitor the variation of food quality in real-time under different supply chain scenarios. Currently, various bespoke models are existing for monitoring of food quality based on the changes in color, image, texture and Near-infrared (NIR) spectra. However, development of food-item specific models by using traditional supervised machine learning techniques to predict the age of the food items would require lot of annotated data per food item. These annotations are expensive as it involves the cost of controlled experimentation and food expertise.

SUMMARY

Embodiments of the present disclosure present technological improvements as solutions to one or more of the above-mentioned technical problems recognized by the inventors in conventional systems. For example, in one embodiment, a processor implemented method of generating a data model for determining remaining shelf-life of a food item is provided. The method involves obtaining via one or more hardware processors, a training data comprising (i) a plurality of images of each food item from among a plurality of food items belonging to a plurality of food categories, and (ii) information on a trend of change of one or more physio-chemical parameters of each food item over a period of time. Further, a state of each of the plurality of food items is determined as one of 'unripe', 'ideally ripe', and 'overly ripe', based on the trend of change of the one or more physio-chemical parameters. Further, the determined state is mapped with a corresponding image from the plurality of images, of each of the plurality of food items. Further, a knowledge graph indicative of a hierarchical taxonomy for the plurality of food categories is generated, wherein the knowledge graph captures a label corresponding to a determined state associated with each of the plurality of images. Further, the data model is trained using the knowledge graph for determining the remaining shelf-life of each of the plurality of food items. The training involves the following steps. Initially, an inductive bias is created by establishing an aging pattern relationship based on similarity of physio-chemical degradation parameters associated with (i) an aging pattern of food items belonging to a food category from among the plurality of food categories and (ii) aging pattern of food items belonging to at least one other food category from among the plurality of food categories, wherein the aging pattern relationship is established using at least one of a zero-shot learning approach or a few-shot learning approach which captures metadata representing the physio-chemical degradation parameters of the food items. Further, the data model is generated based on the label associated with each of the plurality of images, and the established aging pattern relationship.

In another aspect, a system for generating a data model for determining remaining shelf-life of a food item is provided. The system includes one or more hardware processors, a communication interface, and a memory storing a plurality of instructions. The plurality of instructions when executed, cause the one or more hardware processors to initially obtain training data comprising (i) a plurality of images of each food item from among a plurality of food items belonging to a plurality of food categories, and (ii) information on a trend of change of one or more physio-chemical parameters of each food item over a period of time. Further, a state of each of the plurality of food items is determined as one of 'unripe', 'ideally ripe', and 'overly ripe', based on the trend of change of the one or more physio-chemical parameters. Further, the determined state is mapped with a corresponding image from the plurality of images, of each of the plurality of food items. Further, a knowledge graph indicative of a hierarchical taxonomy for the plurality of food categories is generated, wherein the knowledge graph captures a label corresponding to a determined state associated with each of the plurality of images. Further, the data model is trained using the knowledge graph for determining the remaining shelf-life of each of the plurality of food items. The training involves the following steps. Initially, an inductive bias is created by establishing an aging pattern relationship based on similarity of physio-chemical degradation parameters associated with (i) an aging pattern of food items belonging to a food category from among the plurality of food categories and (ii) aging pattern of food items belonging to at least one other food category from among the plurality of food categories, wherein the aging pattern relationship is established using at least one of a zero-shot learning approach or a few-shot learning approach which captures metadata representing the physio-chemical degradation parameters of the food items. Further, the data model is generated based on the label associated with each of the plurality of images, and the established aging pattern relationship.

In yet another aspect, a non-transitory computer readable medium for determining remaining shelf-life of a food item is provided. The non-transitory computer readable medium includes a plurality of instructions, which when executed, cause the one or more hardware processors to perform the following steps for determining the remaining shelf-life of a food item. Initially a training data comprising (i) a plurality of images of each food item from among a plurality of food items belonging to a plurality of food categories, and (ii) information on a trend of change of one or more physio-chemical parameters of each food item over a period of time is obtained. Further, a state of each of the plurality of food items is determined as one of 'unripe', 'ideally ripe', and 'overly ripe', based on the trend of change of the one or more physio-chemical parameters. Further, the determined state is mapped with a corresponding image from the plurality of images, of each of the plurality of food items. Further, a knowledge graph indicative of a hierarchical taxonomy for the plurality of food categories is generated, wherein the knowledge graph captures a label corresponding to a determined state associated with each of the plurality of images. Further, the data model is trained using the knowledge graph for determining the remaining shelf-life of each of the plurality of food items. The training involves the following steps. Initially, an inductive bias is created by establishing an aging pattern relationship based on similarity of physio-chemical degradation parameters associated with (i) an aging pattern of food items belonging to a food category from among the plurality of food categories and (ii) aging pattern of food items belonging to at least one other food category from among the plurality of food categories, wherein the aging pattern relationship is established using at least one of a zero-shot learning approach or a few-shot learning approach which captures metadata representing the physio-chemical degradation parameters of the food items. Further, the data model is generated based on the label associated with each of the plurality of images, and the established aging pattern relationship.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 5A through 5D depict post-harvest variation of ethylene rate overtime at ambient conditions of 20° C. and 80% RH for banana, mango, papaya, and lemon respectively, in an experimental setup, in accordance with some embodiments of the present disclosure.

DETAILED DESCRIPTION

Figure 1:
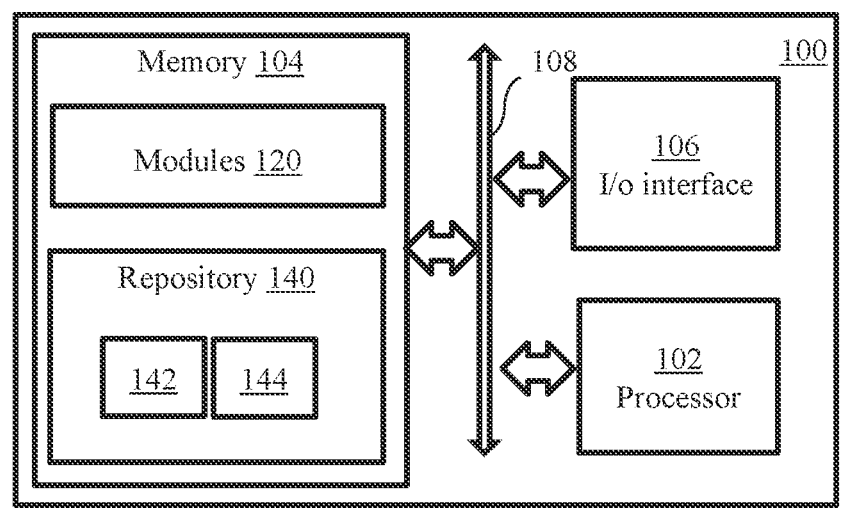
FIG. 1 illustrates an exemplary system for shelf-life prediction of food items according to some embodiments of the present disclosure.

Real-time monitoring and prediction of food quality (or shelf-life) for variety of foods items facilitates in reducing the food wastage which is prevalent globally. Moreover, the monitoring and quality prediction may enable dynamic decisions on rerouting, repurposing, and recycling of food items.

Various solutions available for monitoring of food quality are point solutions. Some of the examples from literature being, prediction of food quality of individual fruit or classification of ripening stages of climacteric fruits like banana, papaya, gooseberry, mango and so on. Even, some work has been done on using machine learning based approach for prediction of yield or pre-harvest leaf borne diseases. However, all these solutions depend only on variation of images for prediction of quality. Currently several known bespoke models are available for monitoring of food quality based on the changes in color, image, texture and Near-infrared (NIR) spectra. Another known technique includes hybrid models built for prediction of quality of individual food items based on the quantitative variation of food attributes such as changes in chemical composition, color, texture, and sensory parameters. These hybrid models are inclusive of physics and artificial intelligence (AI) based models and acts as soft sensors for prediction of food quality in fields along with sensing of minimal parameters in real-time. However, development of food-item specific models by using traditional supervised machine learning techniques to predict the age (or remaining shelf-life) of the food items may require substantial amount of annotated data per food item. Obtaining said annotated data is expensive as it involves a substantial cost of controlled experimentation and food expertise. Moreover, the available systems do not consider important compositional changes and changes in multimodal sensory parameters resulting due to the aging of foods for quality prediction. Moreover, the existing solutions are point specific for specific food items.

Various embodiments described herein include method and system for real-time monitoring and quality prediction of food items by training a generic meta-model for predicting quality for multiple classes/categories of food items. Though, individual food items age differently based on their physio-chemical phenomenon, they share certain visual and sensory characteristics as they perish, and thus can be classified in classes/categories. In an embodiment, the disclosed method utilizes meta-learning techniques which can take advantage of these shared characteristics of the degradation pattern of food items to provide the required generalization for the age prediction task for each of the classes of food items. Meta-learning mechanism may facilitate training of a single model on variety of classes of food items for which small amount of training data is available, such that it can accurately predict the age of food items with no data or limited data. The disclosed system takes into consideration aging properties across distinct foods including physio-chemical properties, sensory parameters and images (visual properties). In an embodiment, the disclosed system implements a hierarchical approach of meta-learning for food-hierarchies, based on the commonalities of the aging properties. Herein, hierarchically structured meta-learning (HSML) algorithm explicitly tailors the transferable knowledge to different clusters of tasks for food hierarchies. The proposed approach not only addresses the challenge via the knowledge customization to different clusters of tasks, but also preserves knowledge generalization among a cluster of similar tasks.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following embodiments described herein.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments.

Referring now to FIG. 1, a block diagram of a system 100 for monitoring and quality prediction of food items is illustrated, according to some embodiments of the present disclosure. The system 100 is capable of training a meta-model (alternately referred to as 'metadata learning model' or 'data model' or 'model') for estimating the quality of food item. Herein, the meta-model is a generic meta-model for food 'shelf-life' prediction that can be trained for prediction of quality of various categories of food items, including but are not limited to, fruits, vegetables, cereals and food grains, fish and meat, and dairy. The meta-model is trained by using a small quantity of training data for each of the categories of the food items that are indicative of aging of food items belonging to that particular category.

The system 100 includes or is otherwise in communication with one or more hardware processors such as a processor 102, at least one memory such as a memory 104, and an I/O interface 106. The processor 102, memory 104, and the I/O interface 106 may be coupled by a system bus such as a system bus 108 or a similar mechanism. The I/O interface 106 may include a variety of software and hardware interfaces, for example, a web interface, a graphical user interface, and the like. The interfaces 106 may include a variety of software and hardware interfaces, for example, interfaces for peripheral device(s), such as a keyboard, a mouse, an external memory, a camera device, and a printer. Further, the interfaces 106 may enable the system 100 to communicate with other devices, such as web servers and external databases. The interfaces 106 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 106 may include one or more ports for connecting a number of computing systems with one another or to another server computer. The I/O interface 106 may include one or more ports for connecting a number of devices to one another or to another server.

The hardware processor 102 may be implemented as one or more microprocessors, microcomputers, microcontrollers, digital signal processors, central processing units, state machines, logic circuitries, and/or any devices that manipulate signals based on operational instructions. Among other capabilities, the hardware processor 102 is configured to fetch and execute computer-readable instructions stored in the memory 104.

The memory 104 may include any computer-readable medium known in the art including, for example, volatile memory, such as static random-access memory (SRAM) and dynamic random-access memory (DRAM), and/or non-volatile memory, such as read only memory (ROM), erasable programmable ROM, flash memories, hard disks, optical disks, and magnetic tapes. In an embodiment, the memory 104 includes a plurality of modules 120 and a repository 140 for storing data processed, received, and generated by one or more of the modules 120. The modules 120 may include routines, programs, objects, components, data structures, and so on, which perform particular tasks or implement particular abstract data types.

Figure 2:
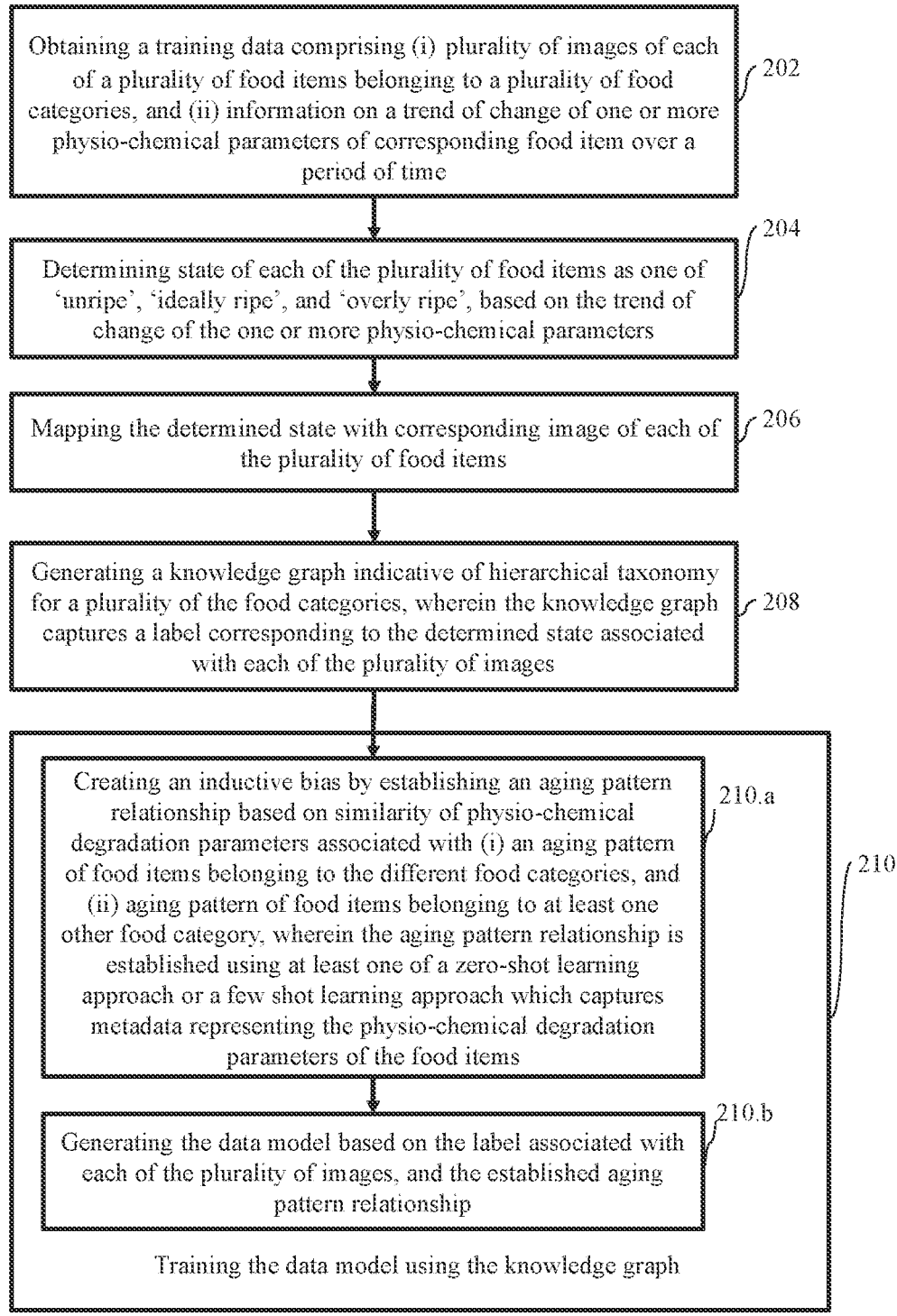
FIG. 2 is a flow diagram of a method for generating a data model for determining remaining shelf-life of a food item, using the system of FIG. 1, according to some embodiments of the present disclosure.
Figure 3:
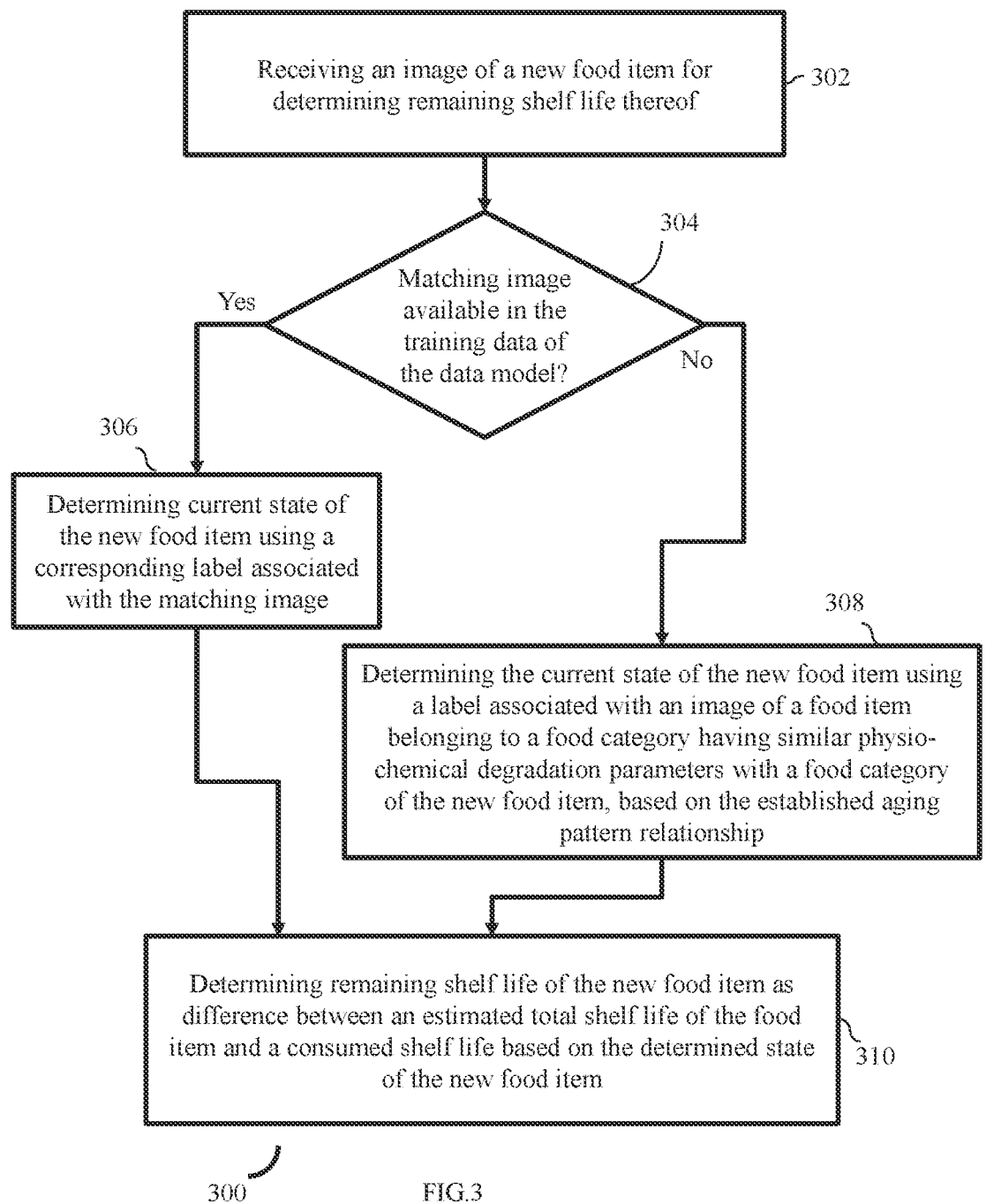
FIG. 3 is a flow diagram of a method of determining the remaining shelf-life of a new food item using the data model, by the system of FIG. 1, according to some embodiments of the present disclosure.

The repository 140, amongst other things, includes a system database 142 and other data 144. The other data 144 may include data generated as a result of the execution of one or more modules in the other modules 120. In an embodiment, the repository 140 may store the training data for training the meta-model. In an embodiment, the training data may include data pertaining to the physio chemical properties of the some of the food items belonging to each of the categories. Said physio-chemical properties may be indicative of aging characteristics of the said some of the food items and correlate with food quality over a period of time. In an embodiment, the physio-chemical properties may be utilized for training the meta model to predict quality of various types of the food items. A method of training the data model is depicted in FIG. 2, and a method of shelf-life prediction of a food item by using the data model embodied in the system (for example, the system 100) is described further with reference to FIG. 3. The steps of the flow diagrams in FIG. 2 and FIG. 3 are explained with reference to the hardware components of the system 100 as depicted in FIG. 1.

FIG. 2 is a flow diagram of a method for generating a data model for determining remaining shelf-life of a food item, using the system of FIG. 1, according to some embodiments of the present disclosure. Operations of the flowchart, and combinations of operation in the flowchart, may be implemented by various means, such as hardware, firmware, processor, circuitry and/or other device associated with execution of software including one or more computer program instructions. For example, one or more of the procedures described in various embodiments may be embodied by computer program instructions. In an example embodiment, the computer program instructions, which embody the procedures, described in various embodiments may be stored by at least one memory device of a system and executed by at least one processor in the system. Any such computer program instructions may be loaded onto a computer or other programmable system (for example, hardware) to produce a machine, such that the resulting computer or other programmable system embody means for implementing the operations specified in the flowchart. It will be noted herein that the operations of the method 200 are described with help of system 100. However, the operations of the method 200 can be described and/or practiced by using any other system.

The data model generated by the system 100 by executing the steps in method 200 is used to process real-time images of food items for determining a state and remaining shelf-life of the food item. In various embodiments, the data model is hosted/stored locally in the electronic device which captures the at least one image using the camera, or in a cloud storage or other means. When the data model is locally hosted, the shelf-life prediction can be done locally in the electronic device. When the data model is hosted on cloud, the at least one image of the food item is transferred to the cloud where it is processed using the data model for the shelf-life prediction. Various steps involved in the process of generating the data model are depicted in FIG. 2.

In a training phase of the data model, at step 202 of the method 200, the system 100 obtains a training data comprising (i) plurality of images of each of a plurality of food items belonging to a plurality of food categories, and (ii) information on a trend of change of one or more physio-chemical parameters of corresponding food item over a period of time. In an example embodiment, the plurality of categories of food items are fruits, vegetables, cereals and food grains, fish and meat, dairy. Each of the classes of food items may follow a hierarchical taxonomy. For example, for the food item category 'fruits', 'fruits' can be classified into climacteric and non-climacteric fruits. Climacteric fruits such as banana, apple, mango, papaya, pear, apricot, peach, plum, avocado, plantain, guava, passion fruit and so on ripens post-harvest when plucked from plants. When these climacteric fruits ages over time, it undergoes variation in color and texture, skin wrinkles, black spots increase and eventually fungus appears on the fruits and finally it becomes degraded. These physical changes can be attributed to the normal physio-chemical aging process of the fruits. Over time there is change in the coloring pigment content like chlorophyll (green), carotenoids (yellow), curcumin (orange), certamen (red) etc. responsible for the color of the fruit and thus the physical color changes. As these climacteric fruits ages, there are certain enzymatic reactions happening in the fruits which causes change in the moisture content, vitamins, proteins, fibers, sugar content, starch content, respiration rate etc. As fruits respires and emits CO2 post-harvest, Ethylene is also emitted in parallel which is responsible for the natural ripening of fruits. So in climacteric fruits, the CO2 respiration rate and ethylene emission rate gradually increases over time until fruits ripen and both the emissions are at the peak when the fruits are ideally ripe for consumption, post which the CO2 and ethylene emission rate starts to decrease implying over ripening and finally degradation of fruits. Unlike climacteric fruits, non-climacteric fruits like strawberry, orange, grapes, lemon, raspberry, cherry, pineapple, watermelon, pomegranate etc. is fully ripe when plucked and the ethylene and CO2 emission from fruits are at the peak and post-harvest both CO2 and ethylene emission rate starts to decrease.

Similarly, in case of vegetables, as they age, some common changes in visual features are change in coloring pigment, texture, growth of mould and fungi. Vegetables also undergoes various enzymatic reactions causing changes in CO2 emission rate, moisture content, vitamins, antioxidants, proteins and minerals. In case of food grains, quality depends on the shape, size and color of grains. Over time, moisture, carbohydrate and protein content changes in food grains causing corresponding variation in food quality.

Considering chicken, fish and meat, over time color changes from pink to grey with the formation of yellow spots. Increase in yellow spot implies rotting of meat. Also, as meat degrades a pungent smell is emitted which can be attributed to the release of ammonia. Also, skin resistance changes, with age the meat becomes sticky and slimy, there are changes in moisture content, protein, nutrients, fat and minerals. In case of dairy products like cheese, milk, curd etc. aging causes growth of mould and fungus, emission of pungent smell due to release of ammonia. Also, the aging of dairy products can be witnesses from the changes in pH, fat and protein content.

As is seen, each of the categories of food items is associated with specific aging pattern and changes in physio-chemical properties. For example, physio chemical properties for the category of fruits may include but are not limited to, visual characteristics including color, mould, fungus; non-invasive characteristics including skin resistance (texture, firmness), C2H4, CO2, invasive characteristics including sugar, vitamins, proteins, fibers, and so on. Similarly, physio chemical properties for the category of poultry, seafood and meat may include but are not limited to, visual characteristics including grey/dark/dull/yellow spots; Non-invasive characteristics including NH3, moisture, skin resistance (sticky, slimy); and Invasive characteristics including Protein, Nutrients, Fat, and minerals. Also, physio chemical properties for the category of vegetables may include but are not limited to, visual characteristics including Chlorophyll, color, fungus; Non-invasive characteristics including CO2, skin resistance; and invasive characteristics including vitamins, antioxidants, protein, minerals. Further, physio chemical properties for the category of cereals may include but are not limited to, visual characteristics including color, size, shape; non-invasive characteristics including Moisture, skin resistance; and invasive characteristics including Carbohydrate, Protein. Furthermore, physio chemical properties for the category of dairy may include but are not limited to, visual characteristics including visual characteristics including mould, fungus; and non-invasive characteristics including NH3, firmness; and invasive characteristics including pH, fat, protein.

Change in values of the physio-chemical parameter over a period of time (wherein span of the period may be pre-defined and configured with the system 100), preferably around the time instance at which the one or more images of the food item (in this example, the fruit) are captured, is referred to as the 'trend of change' of the one or more physio-chemical parameters. Based on the trend of change of the one or more physio-chemical parameters, at step 204, the system 100 determines the state of the food item as one of 'unripe', 'ideally ripe', and 'overly ripe'. It is to be noted that the terms 'unripe', 'ideally ripe', and 'overly ripe' may not be suitable for defining different states of some other categories of food items (for example, meat or diary products), and in such case appropriate terminologies may be used. For explanation purpose, the food category 'fruits' is considered, and the terms 'unripe', 'ideally ripe', and 'overly ripe' are used to define/represent the different states.

Further, at step 206, the system 100 maps the determined state of the food item with corresponding image of each of the plurality of food items. At this step, each of the plurality of images is labeled with the corresponding state.

Further, at step 208, the system 100 generates a knowledge graph indicative of hierarchical taxonomy for a plurality of categories of the plurality of food items, wherein the knowledge graph captures a label corresponding to the determined state associated with each of the plurality of images, such that a sequence of images, arranged in the order they were captured, represent an aging pattern of the food item. The aging patterns identified by the physio-chemical properties for a subset of the each of the food categories may be captured in the knowledge graph. For example, for a fruit category 'fruits', the knowledge graph may include physio-chemical properties of a plurality of physio-chemical degradation parameters associated with few climacteric fruits and few non-climacteric fruits. Such captured properties of the few food items from each category may be utilized for training a meta-model such that the meta-model is trained to predict the aging of entire range of the food items covered in said categories. Further, at step 210, the system 100 trains the data model using the knowledge graph, for prediction of the shelf-life of each of the plurality of food items. The training of the data model using the knowledge graph includes the following steps. At step 210.a, the system 100 creates an inductive bias by establishing an aging pattern relationship based on similarity of physio-chemical degradation parameters associated with (i) an aging pattern of food items belonging to the different food categories, and (ii) aging pattern of food items belonging to at least one other food category, wherein the aging pattern relationship is established using at least one of a zero-shot learning approach or a few shot learning approach which captures metadata representing the physio-chemical degradation parameters of the food items. The inductive bias refers to a set of conditions/statements that help establish the aging pattern relationship. The aging pattern relationship, when established, represents similarities in aging pattern of food items belonging to different food categories. While establishing the aging pattern relationship, the at least one of the zero shot learning approach/mechanism or a few shot learning approach/mechanism may use inter and intra transfer learning approaches to capture the metadata.

Figure 4A:
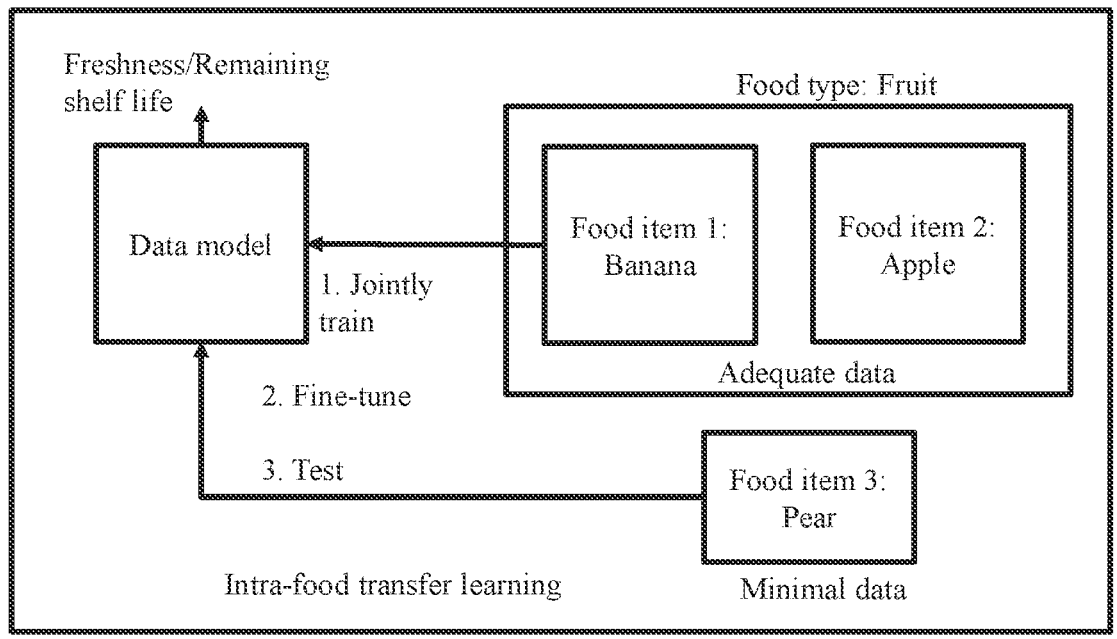
FIGS. 4A and 4B illustrate example process flow for shelf-life prediction of food items using the system of FIG. 1, in accordance with some embodiments of the present disclosure.
Figure 4B:
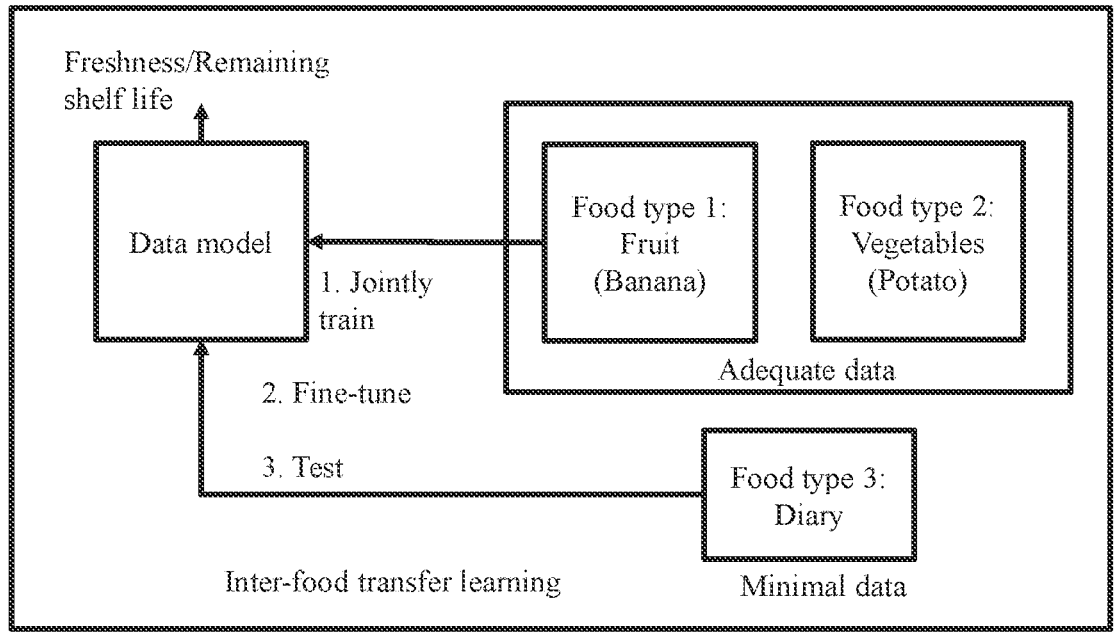

Herein, the system 100 applies the zero-shot or few-shot learning mechanisms to infer the shelf-life of food-items with no or very less data (available training data) for a small subset of foods. In an embodiment, the knowledge graph facilitates in creating the inductive bias for the meta-model by applying zero-shot or few-shot learning techniques. These techniques involve but are not limited to traditional transfer learning techniques. As illustrated in FIGS. 4A and 4B, the system 100 uses the metric-learning or optimization based meta-learning algorithms which allow to train a model on variety of training tasks, such that it can solve a new learning task using small number of training samples, providing good generalizability. In this scenario, prediction of 'age' of individual foods, for which a small amount of training data (5 to 10 samples) is available, serves as a task. As a meta-learning model is trained over variety of such tasks for a set of foods and optimized for best performance on the distribution of tasks, so that it can generalize well for unseen foods, with no or less (1 or 2 samples) data but sharing similar aging properties. As illustrated in FIGS. 4A and 4B, intra food transfer learning implies transfer of knowledge from one food to another within the same class of food with similarity in degradation pattern. For example, transfer of knowledge from one climacteric fruit to another is an example to intra class transfer learning. On the other hand, the inter food transfer learning implies transfer of knowledge from one class of food to another. For example, transfer of knowledge from fruit class to vegetable class based on certain commonalities between the two classes is inter food transfer learning. Further, at step 210.*b*, the system 100 generates the data model based on the label associated with each of the plurality of images, and the established aging pattern relationship.

FIG. 3 is a flow diagram of a method of determining the remaining shelf-life of a new food item using the data model, by the system of FIG. 1, according to some embodiments of the present disclosure.

In an example implementation of the system 100, at step 302 of the method 300, at least one image of a new food item for which the shelf-life is to be determined, is captured using an image capturing device/camera. In an embodiment, the camera is component of an electronic device such as but not limited to a mobile phone, and a tablet PC. In another embodiment, the camera is a standalone equipment, which may or may not have internet connectivity.

Further, the system 100 processes the at least one image using a data model. The training data of the data model may or may not have an image matching the image of the new food item which is checked at step 304. If the training data of the data model has an image matching the image of the new food item (referred to as 'matching image'), then at step 306, the system 100 determines current state of the new food item using a corresponding label associated with the matching image. For example, consider that the label corresponding to the matching image is "ideally ripen". Then the system 100 determines that the state of the new food item is "ideally ripen".

If the training data of the data model does not have a matching image for the captured at least one image of the new food item, then at step 308, then the system 100 determines the current state of the new food item using a label associated with an image of a food item belonging to a food category having similar physio-chemical degradation parameters with a food category of the new food item. At this step, the system 100 determines/identifies the food category having similar physio-chemical degradation parameters with a food category of the new food item, based on the established aging pattern relationship. In an embodiment, after determining the food category having the similar physio-chemical degradation parameters with the food category of the new food item, the system 100 may select/choose an image of one of the food items from that food category, having similarity with the captured at least one image of the new food item. Further, the system 100 determines a state indicated by label associated with the selected image, and then determines the state of the new food item as matching the determined state.

Further, at step 310, the system determines remaining shelf-life of the new food item as difference between an estimated total shelf-life of the food item and a consumed shelf-life based on the determined state of the new food item.

For example, at step 308, the system 100 determines the state (and in turn the aging pattern) of the new food item as one of 'unripe', 'ideally ripe', and 'overly ripe', (assuming the food item is a fruit). In an embodiment, the training data in the data model may contain information on an estimated total shelf-life of each of the plurality of food items, and a consumed shelf-life from each of the states of the food items, which may be decided based on domain knowledge. For example, the estimated shelf-life of a food item may be X, the consumed shelf-life may be Y, then the remaining shelf-life for the food item may be determined by the system 100 as X-Y (wherein value Y may be determined with reference to the determined state of the food item).

The determined remaining shelf-life may be then displayed to a user, using an appropriate user interface on the device (which may be the mobile phone, laptop etc.). This information may further allow the user to decide whether or not to purchase/consume the food item.

Experimental Results:—
Datasets Used:

For the experiments, a dataset of 9 different fruits, namely Guava, Jack-fruit, Lemon, Mango, Papaya, Pear, Pineapple, Pomegranate, and Strawberry, each having few samples labeled into two classes 'good' and 'bad', was used. The data was collected using web-scraping with appropriate keywords to denote the quality of fruits, such as 'good quality mangoes', 'overly ripped guava' or 'papaya which has gone bad', etc. Some of the samples which did not match with the keywords were filtered out, thus handpicking the appropriate 'good' and 'bad' samples. This was done with an assumption that very few samples per class per fruit are present. The number of samples per fruit varied from 36 to 50, having uniform distribution over the classes. Train-validation-test splits were formed by randomly sampling 5-5-remaining data-points per class per fruit for the first experiment and 10-5-remaining data-points per class per fruit for a second experiment. Thus, for a first experiment, the testing was performed on 16 to 40 samples per fruit, whereas for the second experiment the testing is performed on 6 to 20 samples per fruit. Each experiment was repeated 10 times with distinct random splits and the average test accuracy is reported.

Approach:

A Convolution Neural Network (CNN) and a traditional Machine Learning (ML) based approaches was used as baseline. The CNN architecture had 3 convolution layers, with ReLU activation function along with pooling layers and 2 fully connected layers. For the machine learning-based approach color and texture-based features were used. For color-based features, the mean and standard deviation for each of Red Green Blue (RGB), Hue Saturation Value (HSV), and LAB color spaces are calculated. For texture-based features, Grey Level Coherence Matrix (GLCM) is used to extract features like entropy, contrast, etc. To reduce the dimensionality, a Linear Discriminant Analysis (LDA) and further the following models with Voting Classifier for final predictions were used: K-Nearest Neighbors (KNN), Logistic Regression (LR), Support Vector Machines (SVM) and Random Forest (RF). For these baseline approaches, A separate model was built for each fruit in the dataset, using the training and validation (for tuning the hyper-parameters)) data of that fruit and use that model to infer results on the test data of the same fruit.

Further experiments with fruit classification as an objective task were performed, with classes based on its quality such as 'good' and 'bad'. Less number of samples were assumed to have been available per fruit per class. The experiments were geared towards proving the following set-of hypotheses:

H1: For fruit quality classification task, fruit-domain-adapted transfer learning model performs better than pure CNN based approach.

H2: Generic meta-learning-based approach performs better than fruit-specific CNN, ML and fruit-domain-adapted transfer learning approaches.

H3: A meta-model with the fruit-domain-adapted base model performs better than a base model with randomly initialized weights.

H4: A meta-model trained on a specific category of fruits sharing common degradation properties performs better than a more generic meta-model trained on all available fruits.

Experiments:

To validate H1, Resnet18 dataset was finetuned with the domain specific fruits 360 classification dataset. Here the domain is fruits. This data allows to fine-tune the data model for each fruit for the quality classification task, with the small number of training samples available for that fruit. This approach helped get fruit specific models. The splits, cross-entropy loss, Stochastic Gradient Descent (SGD) were used as an optimizer and 0.008 was kept as learning rate. Early stopping was employed for avoiding over-fitting by setting up the patience value to 5. These results were compared against the baselines (CNN and ML).

To validate H2, a meta-learning model was developed using CNN as the base model. The CNN model used was with the same architecture, which was used to create the baseline. An implementation of Model Agnostic Meta-Learning (MAML) algorithm was used. MAML is a popular gradient-based meta-learning algorithm that learns a weight initialization that maximizes task adaptation with few training samples. MAML attempts to learn a parameter initialization for a neural network such that after the model takes small SGD steps, for a particular task's small dataset, it can generalize very well on the task's target set. Learn2learn python library, which provides a high-level MAML implementation in Pytorch, was used.

'Classification of fruit into good and bad classes' served as a task during the experiments. Data for 9 fruits were collected. 8 out of these fruits were used as the training tasks and the remaining one for testing. In experiment 1, 5 samples per class per fruit, of the fruits considered as training tasks for meta-training were used. SGD was used as an optimizer and 0.075 kept as the learning rate. The early stopping mechanism using the validation set of 5 samples per class per fruit was employed for avoiding over-fitting, by setting up the patience value to 5. The resultant meta-model was fine-tuned with the 5 samples per class of the fruit considered as the test task and tested with the remaining samples of that fruit. Experiment 2 repeated the above process with 10 and 5 as training and validation samples per class per fruit, respectively. Average test accuracy of the fruit used was defined as the test task. The results were then compared with the results of the baseline approaches as well as the transfer learning approach (H1). In this setting, multiple models (each trained using all the fruits excluding the fruit for which test results are computed) were used to get test results for each fruit under consideration. However, in a real setting, this approach would give one single generic model for all the fruits.

To validate H3, Resnet18 was fine-tuned on the fruits 360 classification dataset as our base learner model for meta-learning. The rest of the experiments were performed exactly on the similar lines of the experiments performed for H2. The results were compared with results of H1 and H2.

From the literature it is understood that the climacteric fruits exhibit similar physio-chemical degradation trends. Based on this understanding, to validate H4, the fruits were categorized into 5 climacteric fruits namely, Guava, Jack-fruit, Mango, Papaya, and Pear and 4 non-climacteric fruits include Lemon, Pineapple, Pomegranate, and Strawberry. Distinct models were meta-learned for climacteric and non-climacteric fruits and the category-wise meta-model was used to test on the fruits belonging to the respective category. The fruit-domain-adapted Resnet18 was used as the base learner same as discussed for H3, and the same set of experiments as discussed for H2 were followed. The results were compared with H3 to validate if fruit category specific meta-model performs better than a generic meta-model.

Results

TABLE 1

Experiment 1: (5 Train - 5 Validation - Remaining Test)

| Lemon | Pear | Papaya | Mango | Jack-fruit | Guava | Fruits |
|---|---|---|---|---|---|---|
| 50.00 | 49.16 | 48.45 | 49.24 | 49.23 | 47.34 | CNN |
| 59.20 | 62.30 | 57.80 | 84.00 | 60.60 | 59.10 | ML |
| 58.00 | 62.30 | 58.00 | 80.00 | 65.00 | 64.01 | H1 |
| 8.00 | 13.14 | 9.55 | 30.76 | 15.77 | 16.67 | % Imp CNN |
| −1.20 | 0.00 | 0.20 | −4.00 | 4.40 | 4.91 | % Imp ML |
| 73.46 | 72.63 | 63.43 | 88.25 | 65.30 | 58.00 | H2 |
| 49.21 | 47.00 | 31.00 | 79.22 | 30.60 | 22.50 | % Imp CNN |
| 10.30 | 17.00 | 10.00 | 5.05 | 21.22 | −1.86 | % Imp ML |
| 15.46 | 10.33 | 5.43 | 8.25 | 0.30 | −6.01 | % Imp H1 |
| 67.00 | 67.65 | 72.83 | 86.00 | 70.10 | 63 | H3 |
| −8.79 | −6.85 | 14.81 | −2.54 | 7.35 | 8.64 | % Imp H2 |
| 9.00 | 5.35 | 14.83 | 6.00 | 5.10 | −1.01 | % Imp H1 |
| NA | 73.20 | 86.00 | 77.10 | 77.00 | 74 | H4C |
| NA | 5.55 | 13.17 | −10.9 | 6.90 | 11.00 | % Imp H3 |
| 74.20 | NA | NA | NA | NA | NA | H4 NC |
| 7.20 | NA | NA | NA | NA | NA | % Imp H3 |

TABLE 1-continued

Experiment 1: (5 Train - 5 Validation - Remaining Test)

| Average | Strawberry | Pomegranate | Pineapple |
|---|---|---|---|
| 48.65 | 49.18 | 46.01 | 49.24 |
| 62.07 | 52.30 | 66.70 | 54.00 |
| 63.38 | 59.00 | 66.00 | 58.10 |
| 14.73 | 9.82 | 19.99 | 8.86 |
| 1.60 | 6.70 | -0.70 | 4.10 |
| 70.02 | 66.70 | 68.40 | 57.30 |
| 39.70 | 34.20 | 39.08 | 24.50 |
| 10.80 | 27.53 | 2.55 | 6.11 |
| 4.78 | 7.70 | 2.40 | -0.80 |
| 68.32 | 61.27 | 70.00 | 57.00 |
| 0.71 | -8.14 | 2.40 | -0.52 |
| 4.94 | 2.27 | 4.00 | -1.10 |
| 77.46 | NA | NA | NA |
| 51.14 | NA | NA | NA |
| 65.4 | 57.20 | 72.20 | 58.00 |
| 1.58 | -4.07 | 2.20 | 1.00 |

Experiment 2: (10 Train - 5 Validation - Remaining Test)

| Pear | Papaya | Mango | Jack-fruit | Guava | Fruits |
|---|---|---|---|---|---|
| 50.00 | 49.30 | 49.30 | 44.90 | 45.00 | CNN |
| 66.40 | 59.70 | 85.50 | 70.80 | 70.00 | ML |
| 64.00 | 49.50 | 79.00 | 68.00 | 52.50 | H1 |
| 14.00 | 0.20 | 27.90 | 23.10 | 7.50 | % Imp CNN |
| -2.40 | -10.20 | -6.50 | -2.80 | -17.5 | % Imp ML |
| 70.34 | 69.98 | 96.00 | 65.62 | 61.00 | H2 |
| 40.68 | 41.30 | 4.70 | 46.15 | 35.50 | % Imp CNN |
| 5.94 | 17.22 | 12.28 | -7.31 | -12.80 | % Imp ML |
| 6.34 | 20.48 | 17.00 | -2.38 | 8.50 | % Imp H1 |
| 75.64 | 70.56 | 92.00 | 78.12 | 76.00 | H3 |
| 7.54 | 0.82 | -3.80 | 19.04 | 24.60 | % Imp H2 |
| 11.64 | 21.06 | 13.00 | 2.12 | 23.50 | % Imp H1 |
| 84.24 | 75.92 | 93.20 | 83.00 | 74.00 | H4C |
| 8.70 | 4.36 | 1.20 | 4.88 | -2.00 | % Imp H3 |
| NA | NA | NA | NA | NA | H4 NC |
| NA | NA | NA | NA | NA | % Imp H3 |

| Average | Strawberry | Pomegranate | Pineapple | Lemon |
|---|---|---|---|---|
| 48.42 | 51.50 | 51.50 | 50.00 | 44.30 |
| 66.66 | 65.30 | 65.80 | 58.70 | 57.70 |
| 61.87 | 63.00 | 59.63 | 53.00 | 68.20 |
| 13.45 | 11.50 | 8.13 | 3.00 | 23.90 |
| -4.79 | -2.30 | -6.17 | -5.70 | 10.50 |
| 70.25 | 66.22 | 72.80 | 55.50 | 65.50 |
| 44.38 | 28.50 | 46.70 | 18.00 | 47.85 |
| 3.99 | 1.41 | 10.64 | -5.00 | 13.52 |
| 7.35 | 3.22 | 13.17 | 2.50 | -2.70 |
| 75.60 | 67.50 | 74.62 | 72.50 | 73.50 |
| 10.61 | 1.94 | 2.50 | 30.60 | 12.21 |
| 12.85 | 4.50 | 14.99 | 19.50 | 5.30 |
| 82.07 | NA | NA | NA | NA |
| 3.43 | NA | NA | NA | NA |
| 71.36 | 72.00 | 78.54 | 60.50 | 74.40 |
| -0.67 | 4.5 | 3.92 | -12.0 | 0.90 |

Table. 1 and Table, 2 Illustrate the results in terms of test accuracy, averaged over 10 random splits, for all the four hypotheses and compares it with the benchmarks (% improvement in accuracy), for a first experiment and a second experiment respectively. Substantial improvement over the basic CNN model was observed for both H1 (% improvement averaged over all the fruits for Experiment 1: 14.73, Experiment 2: 13.45) and H2 (% improvement averaged over all the fruits for Experiment 1: 3910, Experiment 2: 44.38), validating both H1 and H2. Improvements because of meta-learning (H2) were much more than the ones obtained by transfer learning (H1), further validating H2. Good improvements over ML approaches by meta-learning (H2) (% improvement Experiment 1: 10.80, Experiment 2: 3.94) was observed, whereas the results of transfer learning (H1) are comparable with traditional ML models. For meta-learning-based approach (H2), the improvement in performance over traditional ML models, with an assumption of less number of training samples (Experiment 1: 10.80% improvement) was observed to be more as compared to results obtained when an assumption on the availability of more training data (Experiment 2: 3.94% improvement) was made. A domain-adapted base model (H3) does help for most of the fruits, especially when more number of training samples (10.61% improvement) is assumed. Fruit category specific meta-model (H4) does help for climacteric case (Experiment 1: on an average 5.14% improvement, Experiment 2: on an average 3.43% improvement over H3), whereas doesn't help much for non-climacteric fruits (Experiment 1: on an average 1.58% improvement, Experiment 2: on an average -0.67% improvement over H3). The reason can be, as non-climacteric fruits may not exhibit similar visual degradation properties, not meta-knowledge is captured by the model, which is useful for the unseen tasks (fruits). Category specific meta-models help more when less number of training samples are assumed.

Conclusion:

The experimental results indicated that with the small amount of data taken into consideration, for fruit quality classification task, meta-learning-based approaches performed significantly better as compared to the CNN and ML based benchmark approaches. This proves to be more effective than transfer learning. Also, the meta-learning provided a more generic solution as compared to the point (fruit specific) solutions provided by CNN, ML and transfer learning (H1) based approaches. A meta-model with a base model fine-tuned on domain-specific data served better for only certain fruits. Since climacteric fruits share common degradation properties, a category-specific meta-model, meta-trained on climacteric fruits, demonstrates improved performance for unseen climacteric fruits. However, the same is not true for non-climacteric fruits, as they may not exhibit common physiological degradation phenomena.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method of generating a data model for determining remaining shelf-life of a food item, comprising:
   obtaining, via one or more hardware processors, training data comprising (i) a plurality of images of each food item from among a plurality of food items belonging to a plurality of food categories, and (ii) information on a trend of change of one or more physio-chemical parameters of each food item over a period of time;
   determining, via the one or more hardware processors, a state of each of the plurality of food items as one of 'unripe', 'ideally ripe', and 'overly ripe', based on the trend of change of the one or more physio-chemical parameters;
   mapping, via the one or more hardware processors, the determined state with a corresponding image from the plurality of images, of each of the plurality of food items;
   generating, via the one or more hardware processors, a knowledge graph indicative of a hierarchical taxonomy for the plurality of food categories, wherein the knowledge graph captures a label corresponding to a determined state associated with each of the plurality of images; and
   training, via the one or more hardware processors, the data model using the knowledge graph for determining the remaining shelf-life of each of the plurality of food items, the training comprising:
      creating an inductive bias by establishing an aging pattern relationship based on similarity of physio-chemical degradation parameters associated with (i) an aging pattern of food items belonging to a food category from among the plurality of food categories and (ii) aging pattern of food items belonging to at least one other food category from among the plurality of food categories, wherein the aging pattern relationship is established using at least one of a zero-shot learning approach or a few-shot learning approach which captures metadata representing the physio-chemical degradation parameters of the food items; and
      generating the data model based on the label associated with each of the plurality of images, and the established aging pattern relationship.

2. The method as claimed in claim 1, wherein the trend of change represents one of an upward or a downward change or a constant value of the one or more physio-chemical degradation parameters over the period of time.

3. The method as claimed in claim 1, wherein classification of each of the plurality of food items is modelled as a task in meta learning to capture the metadata.

4. The method as claimed in claim 1, further comprises:
   receiving, via the one or more hardware processes, an image of a new food item for determining the remaining shelf-life thereof;
   performing, via the one or more hardware processors, one of the following, based on a match between the received image and at least one of the plurality of images in the training data for the generated data model:
      determining a current state of the new food item using a corresponding label associated with a matching image in the plurality of images in the training data; or
      determining the current state of the new food item using a label associated with an image of a food item belonging to a food category having similar physio-chemical degradation parameters with a food category of the new food item, based on the established aging pattern relationship; and
   determining, via the one or more hardware processors, the remaining shelf-life of the new food item as a difference between an estimated total shelf-life of the food item and a consumed shelf-life based on the determined state of the new food item.

5. A system for generating a data model for determining remaining shelf-life of a food item, comprising:
   one or more hardware processors;
   a communication interface; and
   a memory storing a plurality of instructions, wherein the plurality of instructions when executed, cause the one or more hardware processors to:
      obtain training data comprising (i) a plurality of images of each food item from among a plurality of food items belonging to a plurality of food categories, and (ii) information on a trend of change of one or more physio-chemical parameters of each food item over a period of time;
      determine a state of each of the plurality of food items as one of 'unripe', 'ideally ripe', and 'overly ripe', based on the trend of change of the one or more physio-chemical parameters;
      map the determined state with a corresponding image from the plurality of images, of each of the plurality of food items;
      generate a knowledge graph indicative of a hierarchical taxonomy for the plurality of food categories, wherein the knowledge graph captures a label corresponding to a determined state associated with each of the plurality of images; and
      train the data model using the knowledge graph for determining the remaining shelf-life of each of the plurality of food items, the training comprising:
         creating an inductive bias by establishing an aging pattern relationship based on similarity of physio-chemical degradation parameters associated with (i) an aging pattern of food items belonging to a food category from among the plurality of food categories and (ii) aging pattern of food items belonging to at least one other food category from among the plurality of food categories, wherein the aging pattern relationship is established using at least one of a zero-shot learning approach or a few-shot learning approach which captures metadata representing the physio-chemical degradation parameters of the food items; and generating the data model based on the label associated with each of the plurality of images, and the established aging pattern relationship.

6. The system as claimed in claim 5, wherein the trend of change represents one of an upward or a downward change or a constant value of the one or more physio-chemical degradation parameters over the period of time.

7. The system as claimed in claim 5, wherein the one of more hardware processors are configured to model classification of each of the plurality of food items as a task in meta learning to capture the metadata.

8. The system as claimed in claim 5, wherein the one of more hardware processors are configured to determine the remaining shelf-life of the food item by:

receiving an image of a new food item for determining the remaining shelf-life thereof;

performing one of the following, based on a match between the received image and at least one of the plurality of images in the training data for the generated data model:

determining a current state of the new food item using a corresponding label associated with a matching image in the plurality of images in the training data; or determining the current state of the new food item using a label associated with an image of a food item belonging to a food category having similar physio-chemical degradation parameters with a food category of the new food item, based on the established aging pattern relationship; and determining the remaining shelf-life of the new food item as a difference between an estimated total shelf-life of the food item and a consumed shelf-life based on the determined state of the new food item.

9. A computer program product comprising a non-transitory computer readable medium having a computer readable program embodied therein, wherein the computer readable program, when executed on a computing device, causes the computing device to:

obtain, via one or more hardware processors, training data comprising (i) a plurality of images of each food item from among a plurality of food items belonging to a plurality of food categories, and (ii) information on a trend of change of one or more physio-chemical parameters of each food item over a period of time;

determine, via the one or more hardware processors, a state of each of the plurality of food items as one of 'unripe', 'ideally ripe', and 'overly ripe', based on the trend of change of the one or more physio-chemical parameters;

map, via the one or more hardware processors, the determined state with a corresponding image from the plurality of images, of each of the plurality of food items;

generate, via the one or more hardware processors, a knowledge graph indicative of a hierarchical taxonomy for the plurality of food categories, wherein the knowledge graph captures a label corresponding to a determined state associated with each of the plurality of images; and train, via the one or more hardware processors, the data model using the knowledge graph for determining the remaining shelf-life of each of the plurality of food items, the training comprising:

creating an inductive bias by establishing an aging pattern relationship based on similarity of physio-chemical degradation parameters associated with (i) an aging pattern of food items belonging to a food category from among the plurality of food categories and (ii) aging pattern of food items belonging to at least one other food category from among the plurality of food categories, wherein the aging pattern relationship is established using at least one of a zero-shot learning approach or a few-shot learning approach which captures metadata representing the physio-chemical degradation parameters of the food items; and generating the data model based on the label associated with each of the plurality of images, and the established aging pattern relationship.

10. The computer program product as claimed in claim 9, wherein the trend of change represents one of an upward or a downward change or a constant value of the one or more physio-chemical degradation parameters over the period of time.

11. The computer program product as claimed in claim 9, wherein the non-transitory computer readable medium further causes the computing device to model classification of each of the plurality of food items as a task in meta learning to capture the metadata.

12. The computer program product as claimed in claim 9, wherein the non-transitory computer readable medium further causes the computing device to determine the remaining shelf-life of the food item by:

receiving an image of a new food item for determining the remaining shelf-life thereof;

performing one of the following, based on a match between the received image and at least one of the plurality of images in the training data for the generated data model:

determining a current state of the new food item using a corresponding label associated with a matching image in the plurality of images in the training data; or determining the current state of the new food item using a label associated with an image of a food item belonging to a food category having similar physio-chemical degradation parameters with a food category of the new food item, based on the established aging pattern relationship; and determining the remaining shelf-life of the new food item as a difference between an estimated total shelf-life of the food item and a consumed shelf-life based on the determined state of the new food item.

\* \* \* \* \*